United States Patent
Rouxel et al.

(10) Patent No.: US 10,288,553 B2
(45) Date of Patent: May 14, 2019

(54) MODULAR PHOTOACOUSTIC DETECTION DEVICE

(71) Applicant: Commissariat A l'Energie Atomique et aux Energies Alternatives, Paris (FR)

(72) Inventors: Justin Rouxel, Brest (FR); Mickael Brun, Eybens (FR); Alain Gliere, Grenoble (FR); Sergio Nicoletti, Sinard (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 164 days.

(21) Appl. No.: 15/174,322

(22) Filed: Jun. 6, 2016

(65) Prior Publication Data

US 2016/0356700 A1  Dec. 8, 2016

(30) Foreign Application Priority Data

Jun. 8, 2015  (FR) ..................... 15 55200

(51) Int. Cl.
*G01N 21/17* (2006.01)
*G01N 29/24* (2006.01)

(52) U.S. Cl.
CPC ..... *G01N 21/1702* (2013.01); *G01N 29/2418* (2013.01); *G01N 29/2425* (2013.01);
(Continued)

(58) Field of Classification Search
CPC ........... G01N 21/1702; G01N 29/2418; G01N 29/2425; G01N 2021/1704;
(Continued)

(56) References Cited

U.S. PATENT DOCUMENTS 4,408,478 A * 10/1983 Bechthold .......... G01N 21/1702
73/24.02
7,304,732 B1 12/2007 Polcawich et al.
(Continued)

FOREIGN PATENT DOCUMENTS

EP       2 515 096 A1    10/2012
WO    WO 03/083455 A1   10/2003

OTHER PUBLICATIONS

Yue et al., A model for the microfabrication with selective laser sintering metal products, Proc. SPIE 5641, MEMS/ MOEMS Technologies and Applications II, (Dec. 30, 2004).*
(Continued)

*Primary Examiner* — Lisa M Caputo
*Assistant Examiner* — Irving A Campbell
(74) *Attorney, Agent, or Firm* — Oblon, McClelland, Maier & Neustadt, L.L.P.

(57) ABSTRACT

Modular photoacoustic detection device comprising:
a photoacoustic cell including at least two chambers connected by at least two capillaries and forming a Helmholtz type differential acoustic resonator;
acoustic detectors coupled to the chambers;
a light source capable of emitting a light beam having at least one wavelength capable of exciting a gas intended to be detected and which can be modulated to a resonance frequency of the photoacoustic cell;
a first photonic circuit optically coupling the light source to an input face of a first of the chambers;
wherein the first photonic circuit is arranged in a detachable manner in a first housing formed in the acoustic cell and emerging on the input face of the first chamber.

15 Claims, 9 Drawing Sheets

(52) U.S. Cl.
CPC ........... *G01N 2021/1704* (2013.01); *G01N 2021/1708* (2013.01); *G01N 2201/0245* (2013.01); *G01N 2291/021* (2013.01); *G01N 2291/02872* (2013.01)

(58) Field of Classification Search
CPC ... G01N 2021/1708; G01N 2201/0245; G01N 2291/021; G01N 2291/02872; G02B 6/12; G02B 6/12007; G02B 6/12011; G02B 6/12014; G02B 6/12016; G02B 6/12019; G02B 6/12021; G02B 6/12164; G02B 6/12161
USPC ................................................ 73/24.02, 643
See application file for complete search history.

(56) References Cited

U.S. PATENT DOCUMENTS

| | | | |
|---|---|---|---|
| 9,335,259 B2 | 5/2016 | Gliere et al. | |
| 9,500,844 B2* | 11/2016 | Jiang | G02B 21/0028 |
| 2008/0138088 A1* | 6/2008 | Welch | H01S 5/026 |
| | | | 398/183 |
| 2009/0174884 A1 | 7/2009 | Kosterev et al. | |
| 2010/0139368 A1 | 6/2010 | Kotovsky et al. | |
| 2012/0151995 A1 | 6/2012 | Schade et al. | |
| 2013/0008229 A1 | 1/2013 | Avramescu et al. | |
| 2013/0039147 A1* | 2/2013 | Witte | A61B 5/0093 |
| | | | 367/7 |

OTHER PUBLICATIONS

Nicoletti, et al. (2014). Challenges in the Design and Fabrication of a Lab-on-a-Chip Photoacoustic Gas Sensor. Sensors (Basel, Switzerland), 14(1), 957-974. http://doi.org/10.3390/s140100957.*

U.S. Appl. No. 14/307,842, filed Jun. 18, 2014, 2014/0376854 A1, Mickael Brun et al.
U.S. Appl. No. 14/857,223, filed Sep. 17, 2015, 2016/0091676 A1, Julien Favreau et al.
P. Karioja, et al., "LTCC based differential photo acoustic gas cell for ppm gas sensing" Proc. of SPIE, Optical Sensing and Detection, vol. 7726, May 13, 2010, pp. 77260H-1-77260H-13.
French Preliminary Search Report dated Mar. 30, 2016 in French Application 15 55200, filed on Jun. 8, 2015 ( with English Translation of Categories of Cited Documents).
S. Nicoletti et al "Challenges in the realization of a fully integrated optical lab-on-chip", IEEE Sensors 2014 Proceedings, 2014, 4 pages.
Alain Gliere et al. "Challenges in the Design and Fabrication of a Lab-on-a-Chip Photoacoustic Gas Sensor", Sensors vol. 14, No. 1, 2014, 18 pages.
J. Rouxel et al. "Development of a miniaturized differential photoacoustic gas sensor", Procedia Engineering, vol. 120, 2015, 4 pages.
A. Gliere et al "A Coupled Model for the Simulation of Miniaturized and Integrated Photoacoustic Gas Detector", Int. J. Thermophys, 2013, 18 pages.
Samara L. Firebaugh et al "Miniaturization and Integration of Photoacoustic Detection with a Microfabricated Chemical Reactor System", Journal of Microelectromechanical System. vol. 10, No. 2, 2001, 4 pages.
Paul M. Pellegrino et al "Miniature Photoacoustic Chemical Sensor Using Microelectromechanical Structures", Chemical and Biological Sensing V, vol. 5416, 2004, 10 pages.
A.V. Gorelik et al. "Application of a miniaturized photoacoustic cell for high-sensitivity laser detection of ammonia in gas media", Phys. 2008, 10 pages.
Ellen Holthoff et al. "Quantum Cascade Laser-Based Photoacoustic Spectroscopy for trace vapor Detection and Molecular Discrimination", Sensors Vo. 10. No. 3, 2010, 17 pages.

* cited by examiner

MODULAR PHOTOACOUSTIC DETECTION DEVICE

TECHNICAL FIELD AND PRIOR ART

The invention relates to the field of miniaturized photoacoustic detection devices, and notably that of miniaturized gas sensors making use of a photoacoustic effect for measuring the concentration of some gaseous elements.

The principle of a measurement of a gas by photoacoustic effect is based on the excitation of an acoustic wave in the gas by a light source such as a pulsed or amplitude or wavelength modulated laser. The wavelength of the radiation, for example in the mid-infrared (MIR), the near-infrared (NIR), or the visible or UV domain, emitted by the laser is chosen to interact specifically with the molecules of the gas to detect. The emission of the light source being modulated, the energy absorbed by the gaseous molecules is restored in the form of a transitory heating which generates a pressure wave, itself measured by an acoustic detector such as a microphone. Although the photoacoustic effect has been known for a long time, its use for gas measurement has been made possible by the implementation of monochromatic light sources such as lasers, and sensitive microphones such as electret capacitive microphones.

Detection is improved by confining the gas in a cavity and by modulating the laser to an acoustic resonance frequency of the cavity. The amplitude of the acoustic wave obtained is directly linked to the concentration of the gaseous compound searched for in the gas present in the excited cavity.

Detection efficiency is based to a large extent on the efficient coupling of the luminous flux of the laser with the gas contained in the resonating cavity because the measured signal is proportional to the energy absorbed, then dissipated, by the gas.

The document WO 03/083455 A1 describes a photoacoustic measurement device making it possible to detect the presence of a gas and comprising a particular structure of photoacoustic cell called "Differential Helmholtz Resonator" (DHR), or Helmholtz type differential acoustic resonator. Such a photoacoustic cell comprises two identical chambers connected together by two capillaries. Acoustic resonance is produced by exciting only one of the two chambers. At resonance, the pressures in the two chambers oscillate in phase opposition. The pressures in the chambers are measured by microphones placed on the walls of the two chambers. With such a resonator, the calculation of the difference between the signals coming from each chamber, which corresponds to the useful signal, makes it possible to increase the amplitude of the measured signal and to eliminate a part of the surrounding noise, and thus to have in the end a good signal to noise ratio.

Such a device nevertheless has the drawbacks of being limited to a non-miniaturized laboratory apparatus, of having limited transmission wavelengths, of being sensitive to temperature variations and to vibrations, and of having significant constraints of positioning and alignment of its elements for its production.

The document EP 2 515 096 A1 describes a photoacoustic gas detection device comprising a DHR type miniaturized photoacoustic resonator integrated on silicon. The structure of this detector is obtained by the implementation of techniques from the microelectronics field in several substrates bonded together. The manufacturing process imposes placing the MIR waveguide, which makes it possible to inject the optical laser signal into one of the two chambers, in the lower part of the central substrate which is thinned to a thickness determined by the height of the chambers. The whole of the device is produced in the form of a single nano-photonic circuit integrating all the elements of the device.

Thus, this device is miniaturized, which has numerous advantages. In fact, this miniaturization makes it possible to have a stronger pressure signal produced by the sensor due to the fact that this signal increases when the size of the resonator is reduced. DHR resonators are particularly well suited to miniaturization and to integration on silicon because they are relatively insensitive to the location of the thermal energy deposition and because, the pressure being practically constant in each chamber, it is possible to multiply the number of microphones per chamber to improve the signal to noise ratio.

On the other hand, the monolithic structure of this device poses several drawbacks.

In fact, after one or more gas detections, the chambers of the photoacoustic cell may be contaminated by the gas or gases detected. It is also possible that the microphones no longer work after several gas detections. Yet, with such a monolithic structure, it is then necessary to replace the whole detection device to carry out new gas detections.

In addition, in order to be able to carry out the detection of different gases, the device necessarily makes use of several different laser sources, which represents a significant cost for the production of the detection device. This is all the more problematic when the contamination of the chambers of the photoacoustic cell imposes the replacement of these different laser sources.

DESCRIPTION OF THE INVENTION

An aim is thus to propose a photoacoustic detection device not posing the problems linked to monolithic detection devices of the prior art, that is to say not requiring a replacement of the whole of the detection device when the chambers of the photoacoustic cell are contaminated by gases, and which can serve in the detection of different gases without having to integrate necessarily different light sources in the device.

For this, a modular photoacoustic detection device is proposed comprising at least:
- a photoacoustic cell including at least two chambers connected by at least two capillaries and forming a Helmholtz type differential acoustic resonator;
- acoustic detectors coupled to the chambers;
- a light source capable of emitting a light beam having at least one wavelength capable of exciting a gas intended to be detected and which can be modulated to a resonance frequency of the photoacoustic cell;
- a first photonic circuit optically coupling the light source to an input face of a first of the chambers;
- wherein the first photonic circuit is arranged in a detachable manner in a first housing formed in the acoustic cell and emerging on the input face of the first chamber.

Thanks to the detachable character of the first photonic circuit, this photoacoustic detection device is modular. Thus, the light source, the first photonic circuit and the photoacoustic cell form elements that can be dismantled from each other and are thus replaceable independently of each other when one of said elements is faulty. For example, if the chambers of the photoacoustic cell are contaminated following a gas detection, only the photoacoustic cell may be replaced and the new photoacoustic cell may be coupled to the other elements of the device which are kept (photonic circuit, light source, etc.). If the light source becomes faulty, it is possible to replace it without having to replace the photoacoustic cell and the first photonic circuit. Similarly, when the acoustic detectors no longer work, it is possible to replace them without having to change the light source and the first photonic circuit.

The modular character of the detection device is also advantageous because it is possible to change easily the light source in order to detect different gases while using the same photoacoustic cell. This avoids having to integrate several different sources in the detection device.

These advantages enable a reduction in the operating costs of the photoacoustic detection device. It is thus possible to mass produce these devices able to serve in the monitoring of gases of atmospheric interest, for example in the prediction of gas leakages in a short time in industry or for the detection of toxic gas for example in airplanes.

The photoacoustic detection device may be qualified as "miniaturized", that is to say having lateral dimensions less than around 10 cm.

A photonic circuit does not correspond to an optic fiber. In fact, a photonic circuit is a circuit produced on a substrate of material, for example made of semiconductor, which is not the case of an optic fiber. Moreover, a photonic circuit has a planar structure, unlike an optic fiber which has a cylindrical structure.

In addition, a photonic circuit may comprise different functionalities. Thus, a photonic circuit may form a circuit multiplexer (with several inputs and one output) and/or demultiplexer. A photonic circuit may also form a collimator and/or fulfil a funnel (or "bundle") function including several inputs and several outputs, which makes it possible to limit the bulk compared to the use of several optic fibers if several wavelengths are emitted by the light source.

In addition, a photonic circuit is well suited for transmitting wavelengths between around 3 and 12 µm, or even between around 3 and 14 µm, which is well suited to carrying out a gas detection. The range of wavelengths which can be transmitted by an optic fiber is more limited than those which can be transmitted by a photonic circuit. For example, optic fibers based on $ZrF_4$ can transmit wavelengths ranging from the visible domain up to around 4.5 µm, and those based on $InF_3$ can transmit wavelengths ranging from the visible domain up to around 6 µm. Optic fibers based on chalcogenide can transmit wavelengths between 1 and 8 µm but they are expensive, fragile and the connections of these fibers are absent or at the best complex to produce.

Optic fibers also pose a problem of bulk compared to a photonic circuit, on account notably of their considerable radius of curvature making their integration difficult. In addition, the sheath of an optic fiber has a minimum size of 125 µm, or even 250 µm, which makes them difficult to bond directly on an input window of a chamber of a photoacoustic cell.

Finally, optic fibers require a greater alignment precision than that required for a photonic circuit.

The acoustic detectors may be coupled in a detachable manner to the photoacoustic cell. Thus, the acoustic detectors may be replaced or kept independently of the photoacoustic cell, thereby increasing the modular character of the device.

The photoacoustic cell may be formed by a stack of several layers of materials. The elements of the cell may be etched in the layers of materials.

According to a first example of embodiment, the photoacoustic cell may comprise at least one stack of a first and of a second layer of material in which may be formed the chambers, the capillaries, the first housing, at least two openings each being able to emerge in one of the capillaries and at least two locations each being able to communicate with one of the chambers and in which the acoustic detectors may be arranged. Such a configuration is particularly suited when the elements of the photoacoustic cell are produced by chemical etching in a part of the thickness of the layers of material.

According to a second example of embodiment, the photoacoustic cell may comprise at least one stack of a first, second, third and fourth layers of material in which may be formed the chambers, the capillaries, the first housing, at least two openings each being able to emerge in one of the capillaries and at least two locations each being able to communicate with one of the chambers and in which the acoustic detectors may be arranged. The fact that the different elements of the photoacoustic cell are produced in the entire thickness of at least one of the layers of the stack makes it possible to obtain patterns having edges clearly perpendicular to each other.

According to a third example of embodiment, the photoacoustic cell may be formed of a monolithic part of sintered powders. Such a cell may be produced by 3D printing.

According to a first example of coupling between the light source and the first photonic circuit, the light source may be optically coupled to an input face of the first photonic circuit by at least one collimation system being able to comprise at least one lens, and the first photonic circuit may form at least one waveguide. This first example of coupling is suited notably when the light source emits a light beam having a single wavelength.

According to a second example of coupling between the light source and the first photonic circuit, the light source may be capable of emitting a light beam having several wavelengths and may be arranged against the first photonic circuit which forms an arrayed waveguide grating multiplexer-demultiplexer circuit.

According to a third example of coupling between the light source and the first photonic circuit, the light source may be optically coupled to an input face of the first photonic circuit by at least one optic fiber, and the first photonic circuit may form at least one waveguide or an arrayed waveguide grating multiplexer-demultiplexer circuit.

The device may further comprise at least one first cooling system capable of thermally adjusting the light source and, when the light source is not arranged against the first photonic circuit, a second cooling system capable of thermally adjusting the photoacoustic cell independently of the light source. The use of two separate cooling systems makes it possible to manage independently the operating temperatures of the light source (temperature for example between around 19° C. and 26° C.) and of the photoacoustic cell (temperature for example between around 15° C. and 20° C.).

The photoacoustic cell may further comprise at least one second housing emerging on an output face of the first chamber, and the device may further comprise at least one second photonic circuit being able to couple optically the output face of the first chamber to an optical detector and arranged in a detachable manner in the second housing. In this configuration, the second photonic circuit thus also forms a part being able to be assembled and/or changed independently of the other elements of the detection device.

The photoacoustic cell may be formed of one or more metals. The use of one or more metals to form the photoacoustic cell enables the walls of the chambers to reflect the light beam, without addition of additional reflection means around the chambers.

The distance between the two capillaries may be equal to around half of the length of at least one of the chambers. This configuration makes it possible to have better pressure homogeneity in the chambers of the photoacoustic cell.

A gas detection device is also proposed, comprising at least one device as described above and gas input and output channels communicating with the chambers of the photoacoustic detection device, and wherein said at least one wavelength of the light beam capable of being emitted by the light source corresponds to at least one absorption wavelength of at least one gas intended to be detected.

A method for producing a modular photoacoustic detection device is also proposed, comprising at least the steps of:
producing at least one photoacoustic cell including at least two chambers connected by at least two capillaries and forming a Helmholtz type differential acoustic resonator;
coupling of acoustic detectors to the chambers;
producing at least one light source capable of emitting a light beam having at least one wavelength capable of making the photoacoustic cell resonate;
producing at least one first photonic circuit arranged in a detachable manner in a first housing formed in the acoustic cell and emerging on an input face of a first of the chambers, and optically coupling the light source to the input face of the first chamber.

BRIEF DESCRIPTION OF THE DRAWINGS

The present invention will be better understood on reading the description of examples of embodiment given for purely indicative purposes and which is in no way limiting while referring to the appended drawings in which.

Identical, similar or equivalent parts of the different figures described hereafter bear the same numerical references so as to make it easier to go from one figure to the next.

The different parts shown in the figures are not necessarily according to a uniform scale, in order to make the figures more legible.

The different possibilities (variants and embodiments) should be understood as not being mutually exclusive and may be combined together.

DETAILED DESCRIPTION OF PARTICULAR EMBODIMENTS

Figure 1:
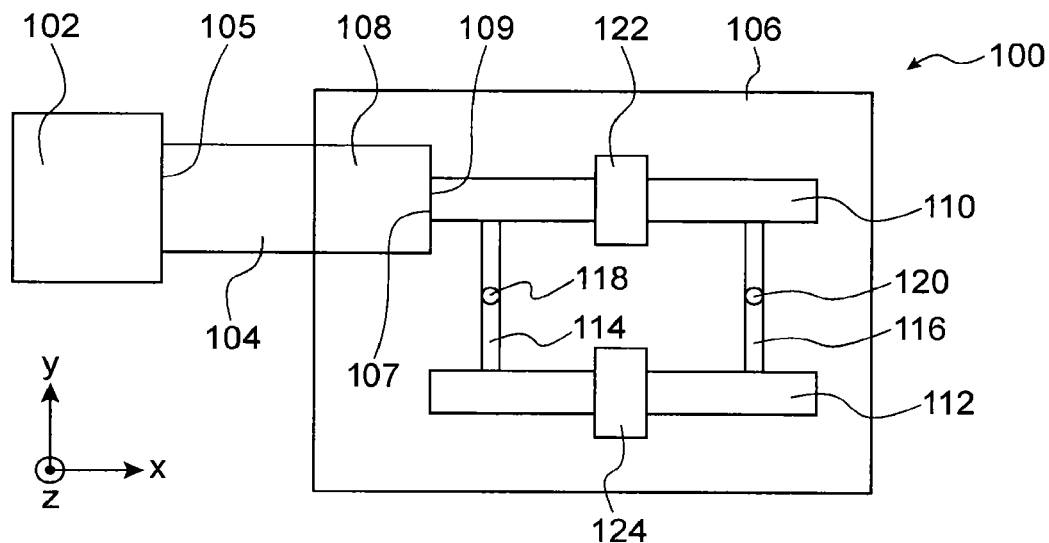
FIG. 1 schematically shows a modular photoacoustic detection device according to a particular embodiment.

Reference is firstly made to FIG. 1 which schematically shows a modular photoacoustic detection device 100 according to a particular embodiment. This device 100 corresponds here to a gas detection device.

The device 100 comprises a light source 102 here corresponding to a laser. This laser may correspond to a QCL (quantum cascade laser) or ICL (interband cascade laser) type laser emitting at least one wavelength in the MIR domain, for example at a wavelength between around 2 µm and 10 µm. Although not shown, the device 100 also comprises an electrical supply of the light source 102 as well as means of modulating the light beam emitted at an acoustic resonance frequency of the cavity in which the light beam is intended to be sent. Compared to the use of a light source which would not be collimated, the use of a light source 102 collimated in the device 100, by virtue of the reduction of the window noise, makes it possible to considerably increase the signal/noise factor, for example by a factor of 2. The window noise corresponds to the parasitic acoustic signal that all the solid parts emit when they are struck by the modulated light wave.

In a variant, the light source 102 may comprise several lasers, and correspond for example to a QCL or ICL laser bar, emitting a light beam formed of several different wavelengths.

The light beam emitted is then transmitted in a first photonic circuit 104 which makes it possible to transmit the light beam in a photoacoustic cell 106 of the device 100. The first photonic circuit 104 comprises an input face 105 optically coupled to the light source 102. The optical coupling between the light source 102 and the first photonic circuit 104 may be produced directly, for example by arranging the light source 102 against the first photonic circuit 104, or via the use of other means which will be described hereafter. The first photonic circuit 104 also comprises an output face 107. The first photonic circuit 104 is inserted in a first housing 108 formed in the cell 106. In FIG. 1, a part of the first photonic circuit 104 comprising the output face 107 is inserted in this first housing 108, and another part of the first photonic circuit 104 is located outside of the first housing 108.

The photoacoustic cell 106 of the device 100 comprises elements corresponding to cavities, or hollowings out, which are:
a first chamber 110 in which the gas to detect is intended to be excited by the light beam emitted by the source 102, and of which an input face 109 intended to receive the light beam is optically coupled to the output face 107 of the photonic circuit 104 (due to the fact that the faces 107 and 109 are parallel with each other and are arranged against each other when the first photonic circuit 104 is inserted in the first housing 108);
a second chamber 112;
two capillaries 114 and 116 making it possible to make the volumes of the chambers 110 and 112 communicate together.

The light source 102 is aligned with the first photonic circuit 104 in order to inject the light into the first chamber 110, without a procedure of alignment of the light source 102 vis-à-vis the first chamber 110 being necessary due to the fact that the insertion of the first photonic circuit 104 in the first housing 108 automatically carries out this alignment.

The capillaries 114, 116 are advantageously connected to the chambers 110, 112 at the level of their lateral faces (faces parallel to the plane (X,Z) shown in FIG. 1). Thus, the capillaries 114, 116 and the chambers 110, 112 may be formed in a same layer, or wafer, of material, which enables their production with a reduced number of manufacturing steps. In a variant, the capillaries 114, 116 may be connected to the chambers 110, 112 at the level of their upper or lower face (faces parallel to the plane (X,Y) shown in FIG. 1), the ends of the capillaries 114, 116 being arranged on or under the chambers 110, 112. In this case, the capillaries 114, 116 and the chambers 110, 112 are made of two separate layers of material.

The height of the capillaries 114, 116 (dimension parallel to the Z axis shown in FIG. 1) is here less than or equal to around half of the height of the chambers 110, 112. This configuration makes it possible to have a resonance frequency of the cell which is low, for example between several hundreds of Hz and several kHz. In addition, this configuration may be obtained when the cell 106 is formed by the stack of two layers of material by producing the capillaries 114, 116 in a part of the thickness of one of these two layers (for example half of the thickness of the layer) and by producing the chambers 110, 112 in a part of the thickness of each of these two layers (for example half of the thickness of each of the layers). Nevertheless, it is also possible to have in a variant capillaries 114, 116 of height substantially equal to that of the chambers 110, 112. In this case, the two layers of the cell 106 may be etched in a similar manner with half of the capillaries 114, 116 and the chambers 110, 112 produced in each of these two layers.

The cell 106 also comprises a first opening 118 emerging in the capillary 114 and making it possible to bring the gas into the chambers 110 and 112 via this capillary 114 and an input channel connected to this first opening 118. The cavity 106 also comprises a second opening 120 emerging in the capillary 116 and making it possible to evacuate the gas outside of the chambers 110 and 112 via this capillary 116 and an output channel connected to this second opening 120. In FIG. 1, the openings 118, 120 are produced substantially at the middle of the length (dimension parallel to the Y axis shown in FIG. 1) of these capillaries 114, 116. In a variant, the second opening 120 may be used to bring the gas into the chambers 110 and 112 via the capillary 116, and the first opening 118 can serve to evacuate the gas outside of the chambers 110 and 112 via the capillary 114.

The cell 106 may be produced from different materials such as semiconductor, for example silicon, glass, plastic, ceramic or instead metal such as for example aluminum, stainless steel, bronze, etc. Stainless steel is particularly advantageous because this metal is inert vis-à-vis gases capable of being sent into the cell 106. The production of a cell 106 made of metal is advantageous because the walls of the chambers 110, 112 may in this case reflect light, which enables this reflected light to again interact with the gas present in the cell 106, and thus to improve the amplitude of the photoacoustic signal.

The device 100 also comprises acoustic detectors 122, 124 such as miniaturized piezoresistive microphones, for example of resonant beam type, or capacitive microphones of vibrating membrane type, are also coupled to the chambers 110, 112 in order to carry out pressure measurements in the chambers 110, 112. Each of the chambers 110, 112 may be coupled to one or more microphones, for example up to eight microphones per chamber. The acoustic detectors 122, 124 are arranged in locations 132, 134 (not visible in FIG. 1) formed in the photoacoustic cell 106 and enabling the acoustic coupling of the detectors 122, 124 to the chambers 110, 112 of the cell 106 as well as the mechanical support of these detectors 122, 124 on the cell 106.

Finally, the device 100 also comprises electronic circuits for processing the signals outputted by the acoustic detectors 122, 124, these circuits not being shown in FIG. 1.

The device 100 described here is modular and comprises a photoacoustic cell 106 provided with the first housing 108 and locations 132, 134 making it possible to couple in a detachable manner, that is to say non-definitively, the first photonic circuit 104 and the acoustic detectors 122, 124 to the chambers 110, 112 of the cell 106. The openings 118, 120 also make it possible to couple in a detachable manner the cell 106 to the separate gas input and output channels of the cell 106.

In a variant, only the first photonic circuit 104 may be coupled in a detachable manner to the cell 106.

The operating principle of the device 100 is similar to that described in the document EP 2 515 096 A1 and is thus not described in detail herein.

The cell 106 is here fastened on a frame, for example made of metal such as aluminum or brass, which is mechanically and thermally decoupled from the light source 102, which makes it possible to manage thermally the cell 106 independently of the light source 102. The light source 102 may thus operate at a very precise temperature which may be different to that of the gas to study located in the cell 106. A first Peltier cooling system (also called Peltier controller or Peltier module), or a water cooling system may be associated with the light source 102 to adjust the operating temperature of the light source 102, whereas a second cooling system, for example a second Peltier module or a second water cooling circuit, may adjust the temperature of the cell 106 where the gas to analyze is present. The device 100 is heterogeneous due to the fact that the cell 106 and the light source 102 do not have the same thermal conductivity. This configuration makes it possible to have good thermal management of the device 100.

The steps of producing the photoacoustic cell 106 according to a first example of embodiment will now be described with regard to FIGS. 2A to 5.

In this first example of embodiment, the cell 106 is formed by the assembly of two metal layers 126, 128 in which are etched, for example by chemical etching, the elements of the cell 106. The metal layers 126, 128 each have here a thickness equal to around 1.5 mm and are for example made of stainless steel.

Figure 2A:
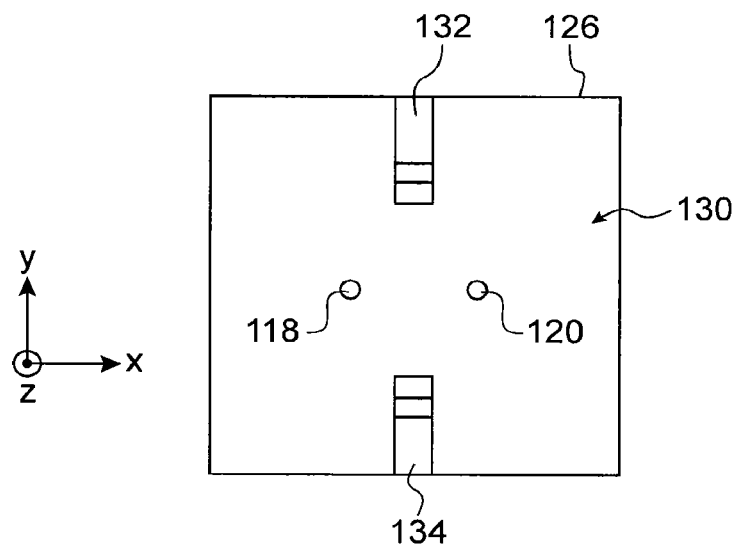
FIGS. 2A to 5 show the steps of producing the photoacoustic cell of a modular photoacoustic detection device according to a first example of embodiment.
Figure 2B:
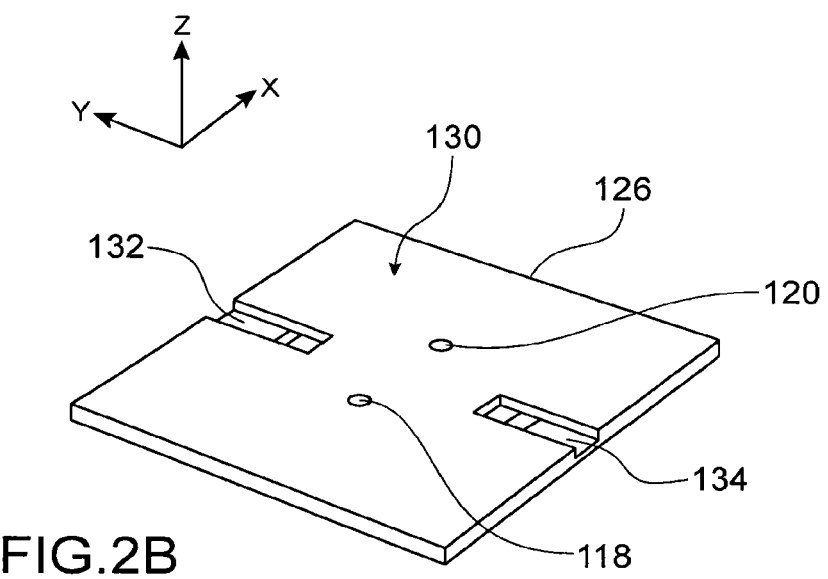

FIG. 2A shows a top view of the first layer 126 in which an upper face 130 of the first layer 126 is visible. FIG. 2B shows a perspective view of the first layer 126 in which the upper face 130 is visible.

The openings 118, 120 are etched through the upper face 130 in a part of the thickness of the first layer 126, here equal to around half of the thickness of the first layer 126, that is to say equal to around 0.75 mm. The diameters of the openings 118, 120 are equal with respect to each other and are equal to the width (dimension parallel to the X axis) of the capillaries 114, 116. The locations 132, 134 intended to receive the acoustic detectors 122, 124 are also etched through the upper face 130 in a part of the thickness of the first layer 126, here also corresponding to around half of the thickness of the first layer 126. These locations 132, 134 form grooves in which the acoustic detectors 122, 124 will be arranged in abutment at the bottom of these grooves.

Fastening holes intended for the tightening of the layers 126, 128 together and to ensure the sealing of the cell 106 are also etched through the entire thickness of the first layer 126. Nine fastening holes, not visible in FIGS. 2A and 2B, are for example produced, five of these holes being intended for the tightening of the layers 126, 128 against each other and four other holes being intended for the support, above the cell 106, of a gas supply device of the cell 106.

Figure 3A:
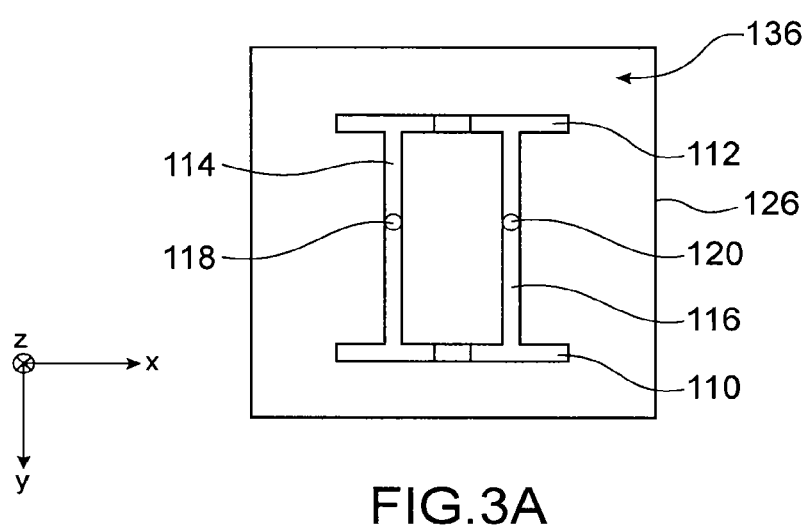
Figure 3B:
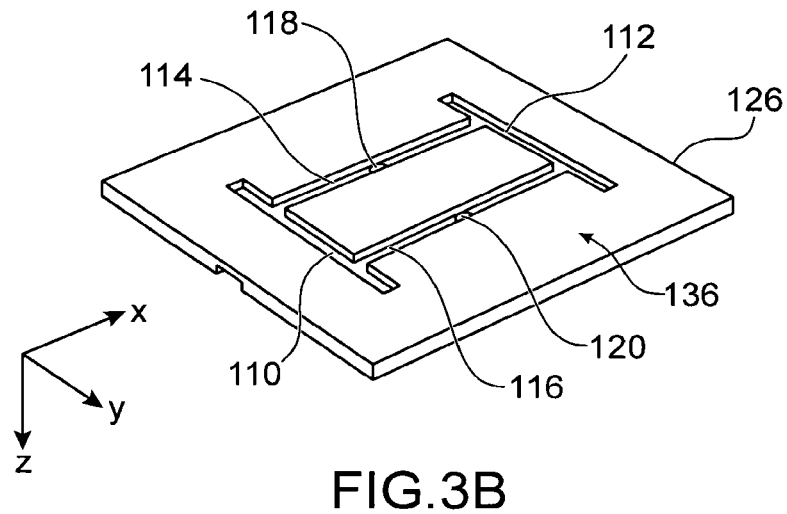

FIG. 3A shows a bottom view of the first layer 126 on which a lower face 136 of the first layer 126 is visible. FIG. 3B shows a perspective view of the first layer 126 in which the lower face 136 is visible.

A first part of the chambers 110, 112 and the capillaries 114, 116 are etched in the form of trenches through the lower face 136 in a part of the thickness of the first layer 126, here equal to around half of the thickness of the first layer 126, that is to say equal to around 0.75 mm. The fastening holes (not visible in FIGS. 3A and 3B) produced through the first layer 126 are thus also present at the level of the lower face 136.

Figure 4A:
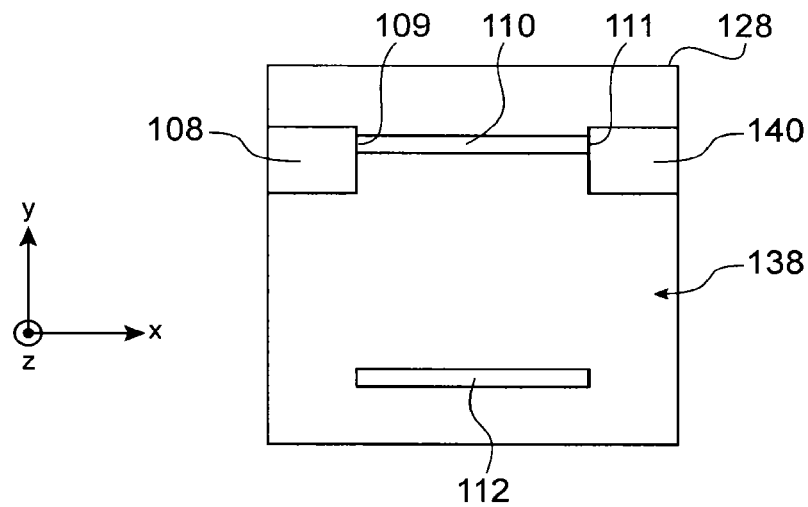
Figure 4B:
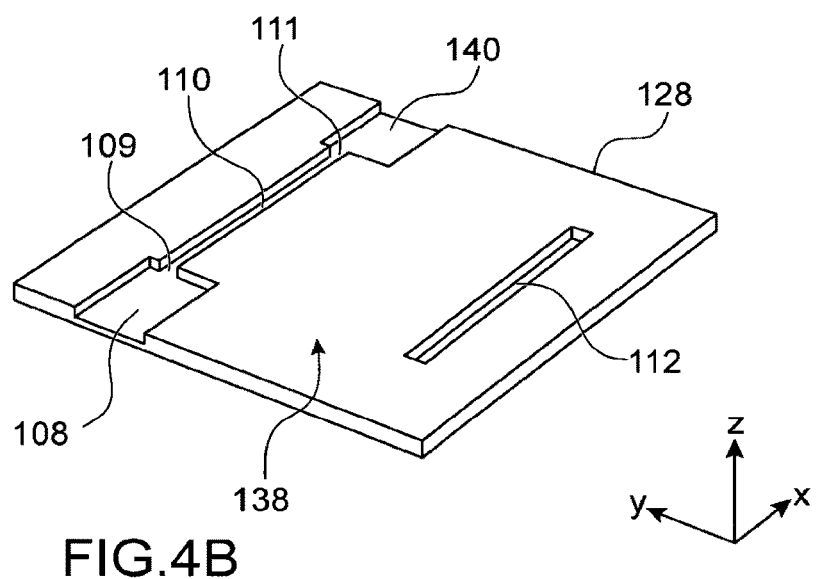

FIG. 4A shows a top view of the second layer 128 in which an upper face 138 of the second layer 128, intended to be arranged against the lower face 136 of the first layer 126, is visible. FIG. 4B shows a perspective view of the second layer 128 in which the upper face 138 is visible.

Trenches intended to form a second part of the chambers 110, 112 are etched through the upper face 138 in a part of the thickness of the second layer 128, here equal to around half of the thickness of the second layer 128, that is to say equal to around 0.75 mm. The first housing 108 in which the first photonic circuit 104 is intended to be inserted is also etched through the upper face 138 in a part of the thickness of the second layer 128, here equal to around half of the thickness of the second layer 128, that is to say equal to around 0.75 mm. The dimensions of the first housing 108 are suited to the first photonic circuit 104 which is intended to be optically coupled to the cell 106. Fastening holes (not visible in FIGS. 4A and 4B) are also produced through the second layer 128. The number, the dimensions and the positioning of these holes correspond to those formed through the first layer 126. A second housing 140 is also etched through the upper face 138 in a part of the thickness of the second layer 128, here equal to around half of the thickness of the second layer 128, that is to say equal to around 0.75 mm. This second housing 140 here has dimensions similar to those of the first housing 108. This second housing 140 is intended to receive a second photonic circuit 146 which will be optically coupled to an output face 111 of the first chamber 110 (opposite to the input face 109 intended to receive the light beam from the first photonic circuit 104) and will make it possible to collect the output light signal having crossed through the first chamber 110 in order to be able for example to check the alignment and the power of the light beam emitted by the source 102. This second housing 140 is nevertheless optional because the device 100 may not comprise this second photonic circuit 146.

Figure 5:
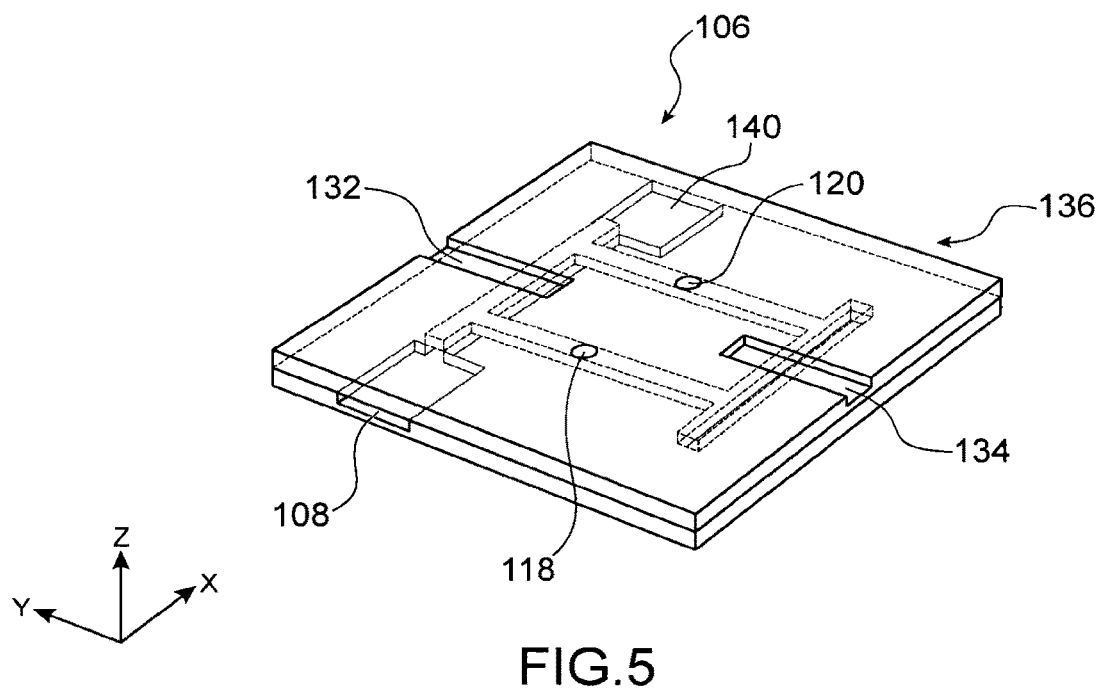

The two layers 126, 128 are then sealed together to form the cell 106, shown in FIG. 5. The stack, or assembly, obtained thus comprises, on the upper face 130 of the first layer 126, the locations 132, 134 intended for the acoustic detectors 122, 124 and the openings 118, 120 for the input and the output of the gas from the cell 106. The housings 108, 140 are accessible from the lateral faces of the cell 106.

The dimensions of the elements of the cell 106 are for example:

chambers 110, 112: length (dimension along the X axis) equal to around 20 mm, width (dimension along the Y axis) equal to around 1.5 mm, and height (dimension along the Z axis) equal to around 1.5 mm;

capillaries 114, 116: length (dimension along the X axis) equal to around 20 mm, width (dimension along the Y axis) equal to around 1.5 mm, and height (dimension along the Z axis) equal to around 0.75 mm;

spacing between the capillaries 114, 116 (dimension parallel to the X axis) equal to around 10 mm;

height (dimension along the Z axis) of the housings 108, 140 equal to around 0.75 mm.

The total volume of the cell 106 is equal to around 135 mm$^3$.

According to a variant of embodiment, the device 100 may comprise chambers 110, 112 not having similar dimensions. In fact, given that the device 100 is a miniaturized device, an opposition of phases may appear between the pressure signals measured in the two chambers 110 and 112 which is imperfect when the dimensions of the chambers 110 and 112 are identical. The subtraction of these two signals which is carried out to obtain the desired measurement is then not optimal. In order to improve this opposition of phases, it is possible that the widths and/or the lengths of the chambers 110 and 112 is different to each other. An optimization by simulation (for example by resolving the equation of the pressure field in the device 100, with chambers 110, 112 of different sizes), for example via a calculation by the finite elements method, leads to the optimal ratio of the dimensions of the chambers 110, 112.

This pressure homogeneity in the chambers 110, 112 also makes it possible to couple a large number of acoustic detectors per chamber and thus have a better signal to noise ratio.

To reduce the pressure difference in the chambers 110, 112, it is also possible to modify the spacing of the capillaries 114, 116. It is thus advantageous that the capillaries 114, 116 are spaced apart by a distance equal to around half of the length of the chambers 110, 112 (which corresponds, for the example described previously, to a spacing of 10 mm between the capillaries 114, 116 for the chambers 110, 112 each of length equal to 20 mm). Consequently, the pressure inhomogeneity in the chambers 110, 112 reduces, and it is possible to increase the number of acoustic detectors coupled to the chambers 110, 112, which makes it possible to improve the signal/noise ratio of the device 100.

Figure 6:
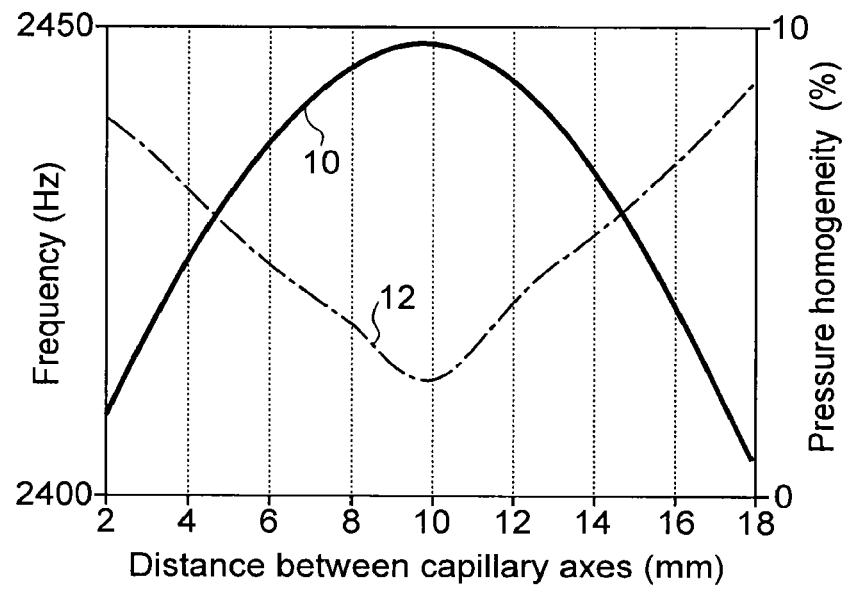
FIG. 6 shows the resonance frequency and the pressure homogeneity in the photoacoustic cell of a modular photoacoustic detection device as a function of the spacing between the capillaries of the photoacoustic cell.

The curve 10 visible in FIG. 6 represents the value of the resonance frequency obtained in the cell 106 as a function of the value of the spacing between the capillaries 114, 116, and the curve 12 represents the pressure homogeneity (the percentage difference between the minimum value and the maximum value of pressure in the chambers 110, 112) as a function of the value of the spacing between the capillaries 114, 116. These data are obtained for chambers 110, 112 of length equal to 20 mm, of width equal to 1.5 mm and height equal to 1.5 mm, and for capillaries 114, 116 of length equal to 20 mm, of width equal to 0.8 mm and height equal to around 1.5 mm, and in the case where the capillaries 114, 116 emerge in the chambers 110, 112 at levels corresponding to around ¼ and ¾ of their length. The curve 12 clearly shows that the best homogeneity is obtained when the capillaries 114, 116 are spaced apart by a distance equal to half of the length of the chambers 110, 112, i.e. 10 mm in the present case.

Figure 7:
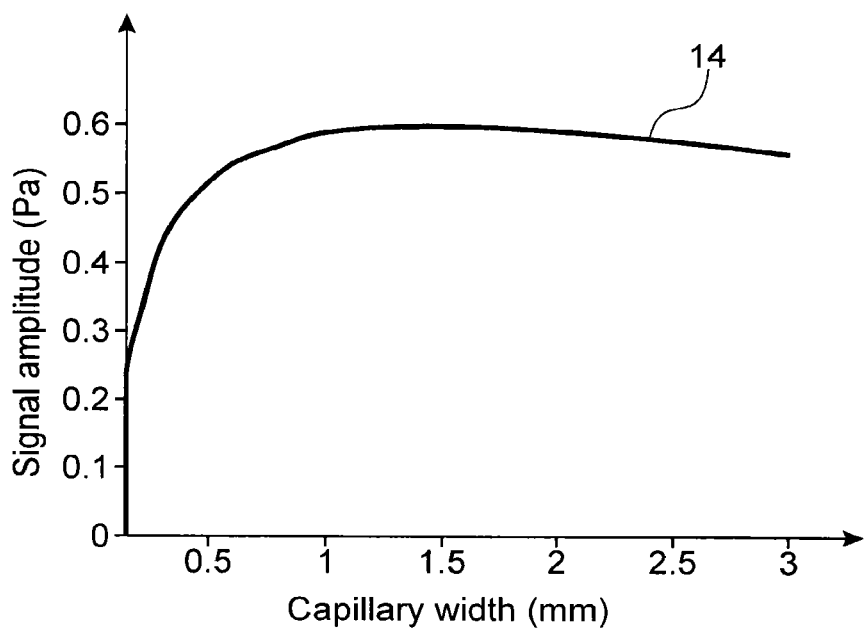
FIG. 7 shows the amplitude of the acoustic signal in the photoacoustic cell of a modular photoacoustic detection device as a function of the width of the capillaries of the photoacoustic cell.

The curve 14 visible in FIG. 7 represents the value of the amplitude of the acoustic signal obtained in the chambers 110, 112 of the cell 106, when the spacing between the capillaries 114, 116 is equal to half of the length of the chambers 110, 112, and by varying the width (dimension along the X axis for the example shown in FIG. 1) of the capillaries 114, 116 with the aim of finding the optimum signal that can be outputted by the acoustic detectors 122, 124. This curve shows that the maximum value of the signal obtained in the cell 106 is obtained when the width of the capillaries 114, 116 is equal to around 1.5 mm.

In the example of FIG. 1 described previously, the openings 118, 120 emerge substantially at the level of the middle of the length of the capillaries 114, 116. In a variant, these openings 118, 120 may be formed at another level than the middle of the length of the capillaries 114, 116, and this may be done without perturbing the symmetry of the flow of the gas in the device 100 if the gas input and output are sufficiently narrow.

To increase the intensity of the signal measured by the acoustic detectors 122, 124 of the device 100, it is possible to produce the capillaries 114, 116 such that they are arranged at the ends of the chambers 110, 112. Such a configuration makes it possible to increase by around 5% the amplitude of the signal measured by the acoustic detectors. However, this increase in the amplitude of the signal occurs to the detriment of the pressure homogeneity which, for its part, reduces, while remaining good.

The different embodiment options described in the document EP 2 515 096 A1, such as for example the use of a Peltier effect, an amplifier integrated in the device, or the different examples of materials described, may apply to the modular photoacoustic detection device described here.

Figure 8A:
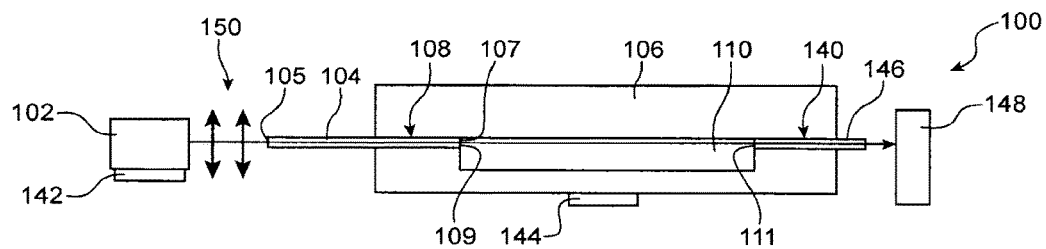
FIGS. 8A to 8C show different coupling configurations between the light source and the first photonic circuit of the modular photoacoustic detection device.
Figure 8B:
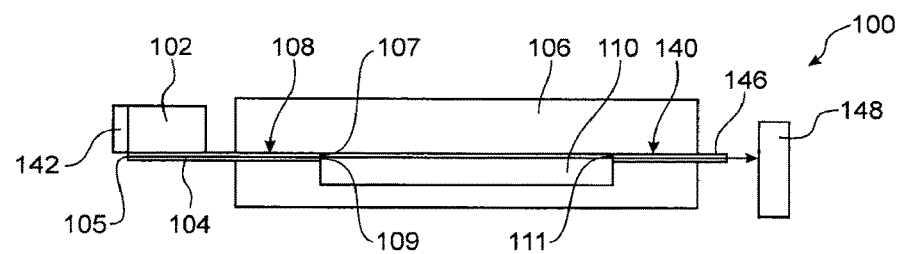
Figure 8C:
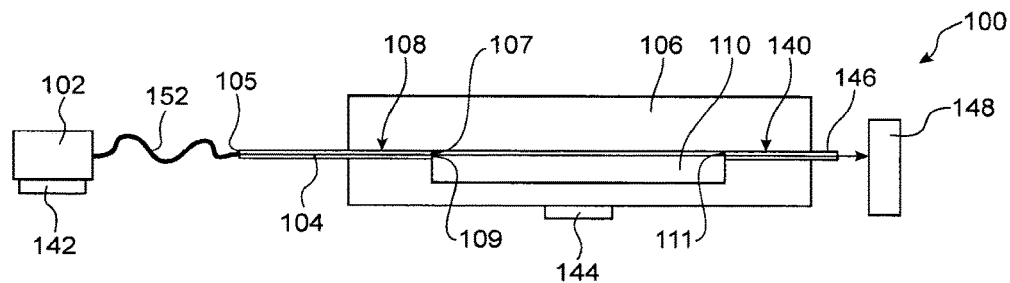

FIGS. 8A to 8C schematically show the device 100 according to different configurations, having different possible couplings between the light source 102 and the first photonic circuit 104.

In these three figures, the device 100 comprises a first Peltier cooling system 142 associated with the light source 102 making it possible to thermally manage the light source 102 independently of the other elements of the device 100. The device 100 also comprises, in the configurations shown in FIGS. 8A and 8C, a second Peltier cooling system 144 associated with a frame (not visible in FIGS. 8A and 8C) on which is arranged the cell 106 and making it possible to thermally manage the cell 106 independently of the other elements of the device 100, notably independently of the light source 102 and making it possible to make the cell 106 work at a temperature different to that of the light source 102.

Moreover, in these three figures, the device 100 comprises a second photonic circuit 146, for example made of silicon, optically coupled to the output face 111 of the first chamber 110 (opposite to the input face 109 intended to receive the light beam from the photonic circuit 104) and making it possible to collect the output light signal having crossed through the first chamber 110 in order to be able for example to check the alignment and the power of the light beam emitted by the source 102. A part of the second photonic circuit 146 is inserted in the second housing 140 formed in the cell 106 such that the output face 111 of the first chamber 110 is directly coupled to this second photonic circuit 146. Finally, the device 100 comprises an optical detector 148 intended to receive the signal from the second photonic circuit 146.

In the first example shown in FIG. 8A, the light source 102 corresponds to a laser source only emitting a single wavelength, for example in the MIR, of which the beam is sent into a collimation system 150 including at least one or even two lenses and making it possible to have at the output a light beam collimated over several centimeters. In fact, a QCL laser emits a laser beam divergent at its output. The collimation system 150 makes it possible to collimate this beam and to reduce its size.

On arriving in the system 150, the beam is collimated with a first correctly positioned lens of focal length f. If the laser source 102 is a point source, it suffices to place the output of the laser source 102 at the focal length of this first lens, which makes it possible to have a beam parallel at the output of the first lens. If the source 102 is not a point source, it is necessary to take into account in this case its shape. Let y1 be the radius of the laser beam and $\theta 1$ the angle of divergence of the beam at the output of the source 102. The collimation of the light of this source 102 by a first lens of focal length f produces a beam of radius $y2=\theta 1*f$ and an angle of divergence $\theta 2=y1/f$. Whatever the lens, the radius and the divergence of the beam depend on each other. For example, to improve the collimation by a factor of two (by reducing the angle by half), it is necessary to multiply the diameter of the beam by two.

In order to reduce the size of the collimated beam, a group of two lenses is used in the system 150. If these two lenses are convergent of respective focal lengths f1 and f2, and if it is wished to reduce the laser beam, the lenses are chosen such that f2<f1. The transversal magnification obtained is given by the formula $G=f2/f1$.

It is also possible to only position a single lens, with in this case the laser placed at the focal length of the lens in order to have a beam at the output of the lens which is collimated.

It is also possible to carry out the collimation and the reduction of the beam using two lenses as may be done with a telescope type mounting, that is to say an afocal system formed of two lenses where the secondary focal point of the first lens coincides with the primary focal point of the second lens, making it possible to create a beam reducer.

To ensure a good coupling between the first photonic circuit 104 and the assembly including the source 102 and the system 150, it is possible to place this assembly on a support being able to control the translations and rotations of the assembly along 3, 5 or 6 axes, thus making it possible to obtain a good positioning of this assembly with respect to the first photonic circuit 104 (which is placed in the first housing 108 and which, as a result, is correctly positioned linearly facing the first chamber 110 of the cell 106).

The collimation system 150 is interposed between the light source 102 and the input face 105 of the first photonic circuit 104 which corresponds, in this first example, to a waveguide suited to the wavelength of the beam emitted by the source 102 and which makes it possible to guide the beam in the first chamber 110. At the output of the first chamber 110, the light beam is still collimated and comes out of the first chamber 110 via the second photonic circuit 146 forming a waveguide or a window that is transparent vis-à-vis the wavelength of the beam.

In this first example, the light source 102 is not in direct contact, or bonded, to the first photonic circuit 104 which itself is mounted in a detachable manner in the first housing 108 of the cell 106. The first cooling system 142 is arranged under the light source 102.

In the second example shown in FIG. 8B, the light source 102 corresponds to a bar of several laser sources or a single laser source. The source 102 is here in direct contact with the first photonic circuit 104 which corresponds to a multiplexer/demultiplexer circuit of AWG (arrayed waveguide grating) type, or arrayed waveguide grating multiplexer/demultiplexer, for example made of Ge or SiGe. The optical coupling between the source 102 and the first photonic circuit 104 is for example obtained via a direct coupling by the edge of the first photonic circuit 104. The source 102 is here integral with the first photonic circuit 104. The length of the first photonic circuit 104 is greater than that of the first housing 108 so that only a part of the first photonic circuit 104 is inserted in the first housing 108 and that the light source 102 is located outside of the cell 106 (this is also the case in the other examples described).

An example of positioning of the source 102 on the first photonic circuit 104 is described below. When the source 102 corresponds to a bar of lasers, the outputs of the bar are positioned facing the inputs of the first photonic circuit 104 using a binocular magnifier. The bar of lasers is placed on a support controlling the translations and rotations of the bar along 3, 5 or 6 axes in order to carry out a preliminary positioning of the bar vis-à-vis the first photonic circuit 104. A camera visualizing the MIR radiations at the output of the first photonic circuit 104 is then used to adjust in a more meticulous manner the positioning of the bar of lasers by playing on the axes of the support. The optimal adjustment is obtained when the camera sees a consequent illumination at the output of the first photonic circuit 104.

This second configuration makes it possible to favor the temperature control of the light source 102, notably when the source 102 corresponds to a bar of several lasers. In fact, due to the fact that the wavelength emitted by each laser varies with the operating temperature of these lasers, it is thus necessary to control the temperature of the bar of lasers. Given that the source 102 is in contact with the first photonic circuit 104 and that this is also in direct contact with the photoacoustic cell 106, it is not possible to independently temperature control the source 102 vis-à-vis the cell 106. If the cell 106 works at a different temperature to that of the source 102, the temperature control of the cell 106 is going to have an influence on the temperature of the source 102. A temperature management of the source 102 is thus favored by associating a cooling system only with the source 102 to ensure the correct operation of the latter. In the third example shown in FIG. 8C, the optical coupling between the light source 102, here of laser type, and the input face 105 of the first photonic circuit 104 is produced by an optic fiber 152. The use of such an optic fiber 152 enables easy control of the light beam, notably concerning its direction. This third example is for example advantageous when the light source 102 is distant and/or not aligned with the photoacoustic cell 106.

When the source 102 corresponds to a single laser, the laser output may be connected to the optic fiber 152. This fiber 152 is placed facing the laser using a support, the aim of which is to ensure optimal coupling between the laser and the fiber 152. This support may correspond to a small plate which is then fastened to the laser when the adjustment is optimal. Once this first coupling has been carried out, a similar coupling is carried out between the other side of the fiber 152 and the input of the first AWG type photonic circuit 104 corresponding to the wavelength of the beam emitted by the laser 102. A support may also be used to align the first photonic circuit 104 with the fiber 152. Once these adjustments have been made, the first photonic circuit 104 is arranged in the first housing 108 facing the first chamber 110. The light thus enters into the cell 106 with a certain divergence. This does not prevent the interaction between the laser and the molecules of gas to detect.

It is possible to use tapers, or progressive connections, at the input of the first photonic circuit 104 in order to facilitate the coupling between the fiber 152 and the laser. In the case of the guided optic, such a taper makes it possible to connect two guides of same thickness but of different section for example by a prism with trapezoidal base.

The first photonic circuit 104 may comprise a pointed-shaped end (at the level of the input face 105), that is to say of width less than that of the remainder of the photonic circuit 104. Such a pointed-shaped end makes it possible to make less divergent the light beam obtained notably at the output of the optic fiber 152, and is advantageous when it is not necessary to collimate the light beam at the input of the first photonic circuit 104.

In the first example of embodiment of the photoacoustic cell 106 described previously with regard to FIGS. 2A to 5, the cell 106 is produced from two metal layers 126, 128 in which are etched the elements of the cell 106. The locations 132, 134, the housings 108, 140, the chambers 110, 112 and the capillaries 114, 116 are etched in a part of the thickness of the metal layers 126, 128.

In a variant, it is possible to implement steps of etching through the entire thickness of the layers of material used to form the cell 106. This implies making use of more than two layers of material to produce the cell 106. Such a second example of embodiment of the cell 106 is described below with regard to FIGS. 9 to 12.

In this second example of embodiment, the photoacoustic cell 106 is produced by an assembly of four layers of material, here four metal layers referenced 154, 156, 158 and 160, in which the different elements of the cell 106 are formed by laser etching. All the etchings carried out in each of these layers 154 to 160 cross through the entire thickness of this layer. In a variant of laser etching, it is possible that a chemical etching is implemented through the entire thickness of these layers.

Figure 9:
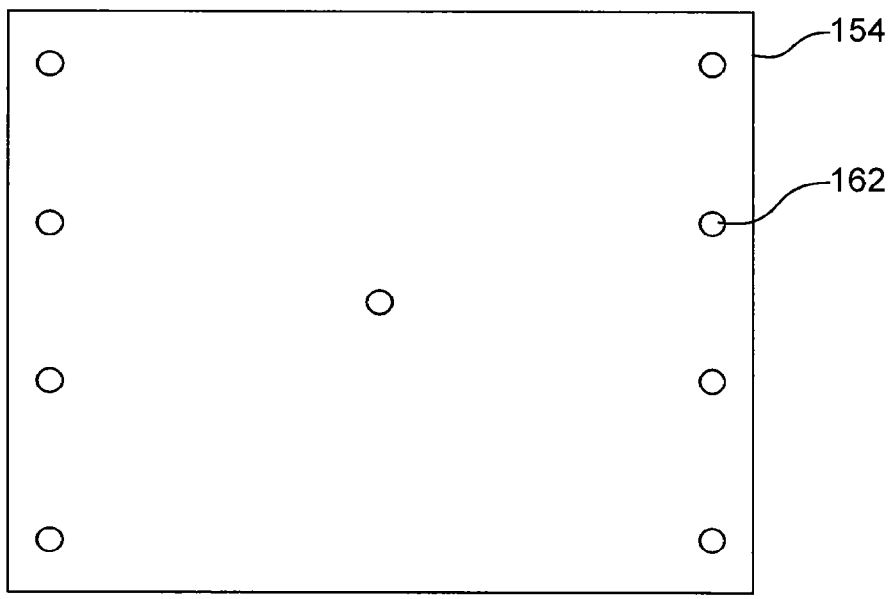
FIGS. 9 to 12 each show a layer of material of a stack forming the photoacoustic cell of a modular photoacoustic detection device according to a second example of embodiment.

The first layer 154 is shown in FIG. 9. This first layer 154 is intended to form the upper cover of the cell 106 and ensure the closing of the upper faces of the capillaries 114, 116. Nine fastening holes 162 are etched through the entire thickness of the first layer 154, this thickness being for example equal to around 0.5 mm.

Figure 10:
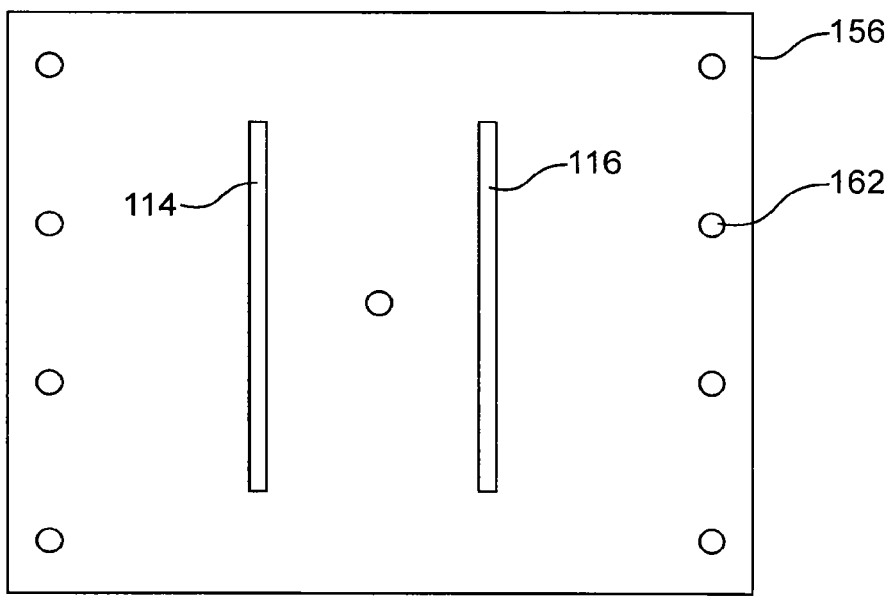

The second layer 156 is shown in FIG. 10. This second layer 156 is crossed through by two slender openings forming the capillaries 114, 116. It is also crossed through by the fastening holes 162. When the first layer 154 is arranged on the second layer 156, the capillaries 114, 116 are thus closed, at the level of the face of the second layer 156 which is in contact with the first layer 154, by the first layer 154. The thickness of the second layer 156 is for example equal to around 0.5 mm.

Figure 11:
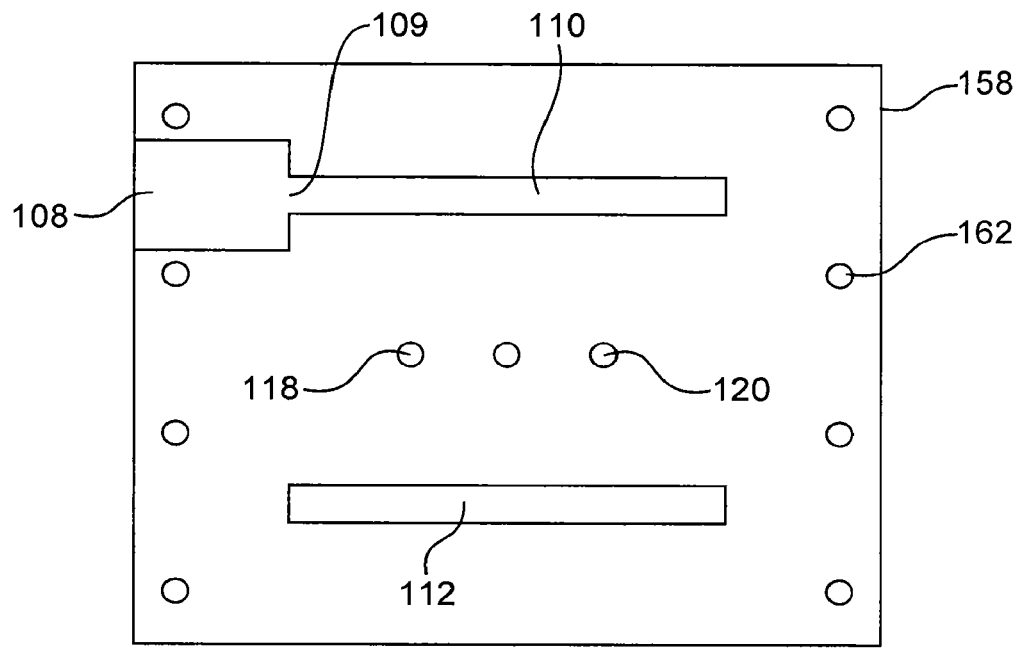

The third layer 158 is shown in FIG. 11. This third layer 158 is crossed through by two slender openings forming the chambers 110, 112. It is also crossed through by another opening intended to form the first housing 108 into which the first photonic circuit 104 will be inserted (in this example, the cell 106 does not comprise the second housing 140). Two other holes are formed through the third layer 158 to form the openings 118, 120 serving for bringing in and evacuating the gas in the cell 106. Finally, the fastening holes 162 are also produced through this third layer 158. The thickness of this third layer 158 is of the order of the thickness of the first photonic circuit 104, advantageously around 0.72 mm, that is to say the typical thickness of a silicon substrate. The third layer 158 is arranged against the face of the second layer 156 opposite to that arranged against the first layer 154, that is to say such that the second layer 156 is arranged between the first layer 154 and the third layer 158. By thus positioning the third layer 158 against the second layer 156, the gas input and output openings 118, 120 are positioned just above the capillaries 114, 116. This third layer 158 also makes it possible to close the capillaries 114, 116 at the level of the face of the second layer 156 which is in contact with the third layer 158. In addition, the chambers 110, 112 and the first housing 108 are closed, at the level of the face of the third layer 158 which is in contact with the second layer 156, by the second layer 156. Finally, when the third layer 158 is thus arranged against the second layer 156, each of the capillaries 114, 116 communicates with the chambers 110, 112.

Figure 12:
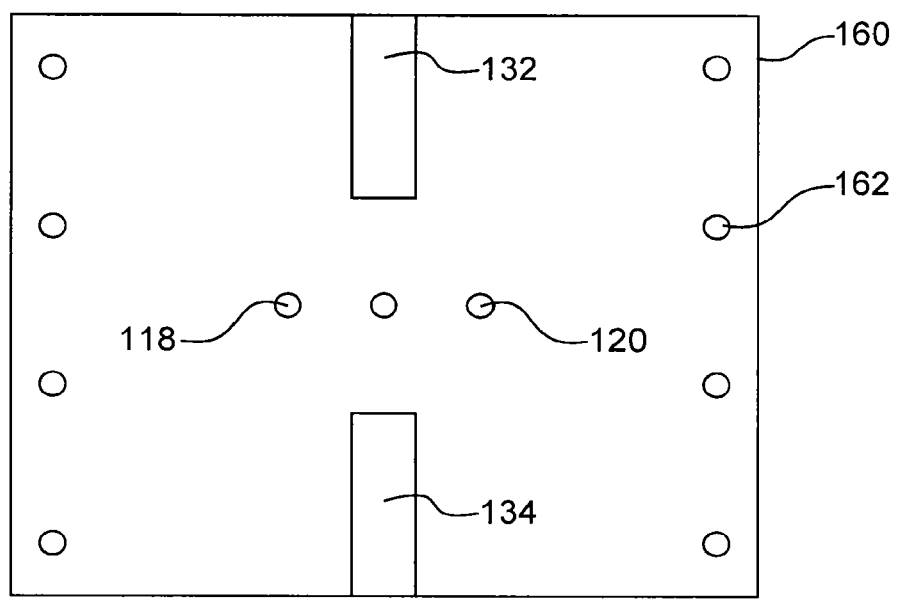

The fourth layer 160 is shown in FIG. 12. This layer 160 is crossed through by the openings 118, 120, by the fastening holes 162, as well as by two other openings intended to form the locations 132, 134 for the acoustic detectors 122, 124. This fourth layer 160 closes the chambers 110, 112 and the first housing 108 at the level of the face of the third layer 158 which is in contact with this fourth layer 160. The thickness of the fourth layer 160 is for example equal to around 0.5 mm.

For the production of the photoacoustic cell 106, the four layers 154, 156, 158 and 160 are assembled against each other as described above, then fastened for example by four screws arranged in the fastening holes 162 situated at the corners of the stack of layers. A central screw may be arranged in the fastening hole 162 located at the center of the cell 106, making it possible to make the cell 106 integral with a frame. An additional mechanical part comprising gas input and output channels enabling the input and the output of the gas to analyze in the cell 106, is for example arranged on the cell 106. O-rings are arranged between the fourth layer 160 of the cell 106 and this additional part. The assembly is then tightened by four other screws to the frame via the four remaining fastening holes 162, which ensures all the more a maintaining of the cell 106 to the frame.

In this second example of embodiment of the photoacoustic cell 106, the dimensions of the chambers 110, 112 are for example equal to around 20 mm (length)*0.75 mm (width) *0.72 mm (height), and the dimensions of the capillaries 114, 116 are for example equal to around 20 mm (length) *0.5 mm (width)*0.5 mm (height). The openings 118, 120 each have for example a diameter equal to around 0.3 mm. Finally, the dimensions of the housing 108 are for example equal to around 6 mm (width)*7.5 mm (length) *0.72 mm (height).

Figure 13:
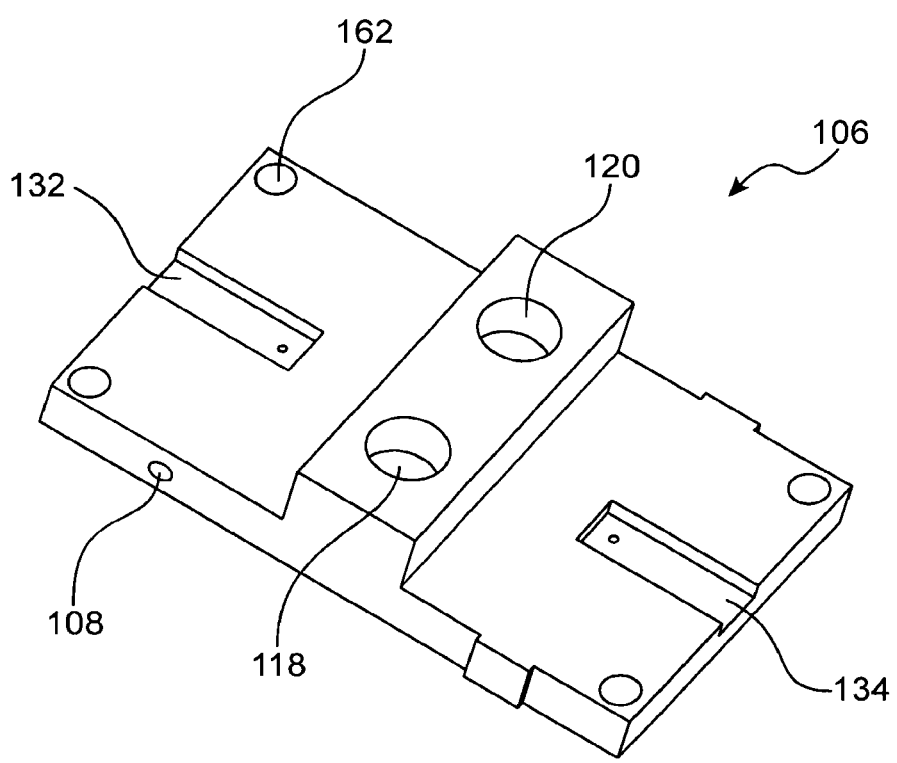
FIG. 13 shows a photoacoustic cell of a modular photoacoustic detection device according to a third example of embodiment.

According to a third example of embodiment of the photoacoustic cell 106, it may be produced by 3D printing using metal powders sintered from a $CO_2$ laser, also called DMLS for Direct Metal Laser Sintering. FIG. 13 schematically shows a photoacoustic cell 106 produced by such a method. This method makes it possible to produce the cell 106 with optimal precision thanks to the production of layers of thickness equal to around 0.02 mm and with a very good resolution of details as well as excellent mechanical properties. Such a technique may be implemented with different metals such as stainless steel, an alloy of chromium and cobalt, aluminum, titanium or super-alloys such as those sold under the tradename Incolnel®. The photoacoustic cell 106 obtained with this method corresponds to a monolithic part.

The invention claimed is:

1. A modular photoacoustic detection device comprising at least:
   a photoacoustic cell including at least two chambers connected by at least two capillaries and forming a Helmholtz type differential acoustic resonator;
   acoustic detectors coupled to the chambers;
   a light source capable of emitting a light beam having at least one wavelength capable of exciting a gas intended to be detected and which can be modulated to a resonance frequency of the photoacoustic cell;
   a first photonic circuit optically coupling the light source to an input face of a first of the chambers, wherein
   the first photonic circuit is arranged in a detachable manner in a first housing formed in the photoacoustic cell and emerging on the input face of the first chamber,
   the photoacoustic cell comprises at least one stack of a first and of a second layer of material in which are formed the chambers, the capillaries, the first housing, at least two openings each emerging in one of the capillaries and at least two locations each communicating with one of the chambers and in which the acoustic detectors are arranged,
   the locations are formed in a part of a thickness of the first layer and cross through an upper face of the first layer,
   the openings cross through an entire thickness of the first layer,
   a first part of each of the chambers is formed in a part of the thickness of the first layer and crosses through a lower face of the first layer opposite to the upper face of the first layer,
   the capillaries are formed in a part of the thickness of the first layer and cross through the lower face of the first layer,
   a second part of each of the chambers is formed in a part of a thickness of the second layer and crosses through an upper face of the second layer which is arranged against the lower face of the first layer, the first and second parts of each of the chambers being arranged facing each other, and
   the first housing is formed in a part of the thickness of the second layer and crosses through the upper face of the second layer.

2. A device according to claim 1, wherein the acoustic detectors are coupled in a detachable manner to the photoacoustic cell.

3. A device according to claim 1, wherein the photoacoustic cell comprises at least one stack of the first and second, and a third and fourth layers of material in which are formed the chambers, the capillaries, the first housing, the at least two openings each emerging in one of the capillaries and the at least two locations each communicating with one of the chambers and in which the acoustic detectors are arranged.

4. A device according to claim 3, wherein:
   the capillaries cross through an entire thickness of the second layer, the first and third layers between which is located the second layer forming upper and lower walls of the two capillaries;
   the chambers and the first housing cross through an entire thickness of the third layer, the second and fourth layers between which is located the third layer forming upper and lower walls of the chambers and of the first housing;
   the locations cross through an entire thickness of the fourth layer;
   the openings cross through the entire thickness of the third and fourth layers.

5. A device according to claim 1, wherein the photoacoustic cell is formed of a monolithic part of sintered powders.

6. A device according to claim 1 wherein the light source is optically coupled to an input face of the first photonic circuit by at least one collimation system comprising at least one lens, and wherein the first photonic circuit forms at least one waveguide.

7. A device according to claim 1, wherein the light source is capable of emitting a light beam having several wavelengths and is arranged against the first photonic circuit which forms an arrayed waveguide grating multiplexer-demultiplexer circuit.

8. A device according to claim 1, wherein the light source is optically coupled to an input face of the first photonic circuit by at least one optic fiber, and wherein the first photonic circuit forms at least one waveguide or an arrayed waveguide grating multiplexer-demultiplexer circuit.

9. A device according to claim 1, further comprising at least one first cooling system capable of thermally adjusting the light source and, when the light source is not arranged against the first photonic circuit, a second cooling system capable of thermally adjusting the photoacoustic cell independently of the light source.

10. A device according to claim 1, wherein the photoacoustic cell further comprises at least one second housing emerging on an output face of the first chamber, and further comprising at least one second photonic circuit optically coupling the output face of the first chamber to an optical detector and arranged in a detachable manner in the second housing.

11. A device according to claim 1, wherein the photoacoustic cell comprises one or more metals.

12. A device according to claim 1, wherein a distance between the two capillaries is equal to around half of the length of at least one of the chambers.

13. A gas detection device, comprising at least one device according to claim 1 and gas input and output channels communicating with the chambers of the photoacoustic detection device, and wherein said at least one wavelength of the light beam capable of being emitted by the light source corresponds to at least one absorption wavelength of at least one gas intended to be detected.

14. A method for producing a modular photoacoustic detection device, comprising:
    producing at least one photoacoustic cell including at least two chambers connected by at least two capillaries and forming a Helmholtz type differential acoustic resonator;
    coupling of acoustic detectors to the chambers;
    producing at least one light source capable of emitting a light beam having at least one wavelength capable of making the photoacoustic cell resonate;
    producing at least one first photonic circuit arranged in a detachable manner in a first housing formed in the photoacoustic cell and emerging on an input face of a first of the chambers, and optically coupling the light source to the input face of the first chamber, wherein the photoacoustic cell comprises at least one stack of a first and of a second layer of material in which are formed the chambers, the capillaries, the first housing, at least two openings each emerging in one of the capillaries and at least two locations each communicating with one of the chambers and in which the acoustic detectors are arranged,
    the locations are formed in a part of a thickness of the first layer and cross through an upper face of the first layer,
    the openings cross through an entire thickness of the first layer,
    a first part of each of the chambers is formed in a part of the thickness of the first layer and crosses through a lower face of the first layer opposite to the upper face of the first layer,
    the capillaries are formed in a part of the thickness of the first layer and cross through the lower face of the first layer,
    a second part of each of the chambers is formed in a part of a thickness of the second layer and crosses through an upper face of the second layer which is arranged against the lower face of the first layer, the first and second parts of each of the chambers being arranged facing each other, and
    the first housing is formed in a part of the thickness of the second layer and crosses through the upper face of the second layer.

15. A method according to claim 14, wherein:
    the production of the photoacoustic cell comprises production of at least one stack of the first and of the second layer of material in which are formed, by chemical etching implemented in a part of the thickness of each of the first and second layers, the chambers, the capillaries, the first housing, the at least two openings each emerging in one of the capillaries and the at least two locations each communicating with one of the chambers and in which the acoustic detectors are arranged, or
    the production of the photoacoustic cell comprises the production of at least one stack of the first and second, and a third and fourth layers of material in which are formed, by chemical etching or laser implemented in an entire thickness of each of the second, third and fourth layers, the chambers, the capillaries, the first housing, the at least two openings each emerging in one of the capillaries and the at least two locations each communicating with one of the chambers and in which the acoustic detectors are arranged, or
    the photoacoustic cell is formed of a monolithic part of sintered metal powders obtained by 3D printing.

* * * * *